United States Patent [19]
Comins et al.

[11] Patent Number: 5,475,108
[45] Date of Patent: Dec. 12, 1995

[54] CAMPTOTHECIN INTERMEDIATES AND METHOD OF MAKING CAMPTOTHECIN AND COMPTOTHECIN ANALOGS

[75] Inventors: Daniel L. Comins, Cary; Matthew F. Baevsky, Chapel Hill, both of N.C.

[73] Assignee: North Carolina State University, Raleigh, N.C.

[21] Appl. No.: 114,475

[22] Filed: Aug. 31, 1993

[51] Int. Cl.$^6$ .............................................. C07D 491/052
[52] U.S. Cl. .............................. 546/41; 546/48; 546/153; 546/180
[58] Field of Search ........................................ 546/41, 48

[56] References Cited

U.S. PATENT DOCUMENTS

| | | | |
|---|---|---|---|
| 4,894,456 | 1/1990 | Wall et al. | 546/41 |
| 5,162,532 | 11/1992 | Comins et al. | 546/48 |
| 5,212,317 | 5/1993 | Comins et al. | 546/301 |
| 5,342,947 | 8/1994 | Lackey et al. | 546/41 |

FOREIGN PATENT DOCUMENTS 0325247  7/1989  European Pat. Off. .

OTHER PUBLICATIONS

S. F. Martin et al., *Efficacious Modification of the Mitsunobu Reaction for Inversions of Sterically Hindered Secondary Alcohols* Tetrahedron Letters 32, 3017–3020 (1991).
M. Saiah et al. *The Use of Chloroacetic Acid in the Mitsunobu Reaction* Tetrahedron Letters 33, 4317–4320 (1992).
J. C. Estevez, et al., *Tributyltinhydride–Induced Intramolecular Radical Cyclization to Aporphines and 5–Oxoaporphines* Tetrahedron Letters 32, 529–530 (1991).
F. E. Ziegler et al., *A New Route to 9,9a–Dihydro–3H–pyrrolo[1,2–a]indoles via Radical Cyclization* J. Org. Chem. 56, 3479–3486 (1990).
Natural Products Chemistry 2, *Synthesis of Camptothecin* 358–361 (1975).
Natural Products Chemistry 3 *Biosynthesis of Camptothecin* 573–574 (1975).
R. E. Lyle et al., *The Synthesis of an Analog of Camptothecin by a General Method* J. Org. Chem. 38, 3268–3271 (1973).
R. E. Lyle et al., *Benzylic Halogenation of Methylquinolines* J. Org. Chem. 24, 3967–3968 (1972).
R. E. Lyle et al., Abstracts, 23d International Congress of Pur and Applied Chemisty (Boston, Mass. 1971) p. 67.

*Primary Examiner*—Donald G. Daus
*Attorney, Agent, or Firm*—Bell, Seltzer, Park & Gibson

[57] ABSTRACT

Disclosed are new methods of making camptothecin and camptothecin analogs defined by Formula I:

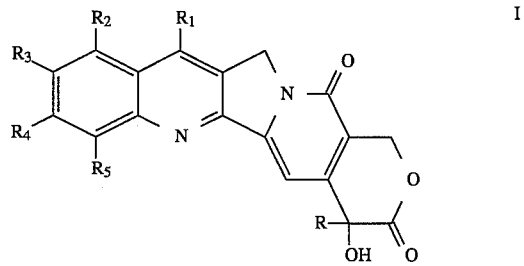

wherein R is loweralkyl; $R_1$ is H, loweralkyl, loweralkoxy, or halo; and $R_2$, $R_3$, $R_4$ and $R_5$ are each independently H, amino, hydroxy, loweralkyl, loweralkoxy, loweralkylthiol, di(loweralkyl)amino, cyano, methylenedioxy, formyl, nitro, halo, trifluoromethyl, aminomethyl, azido, amido, hydrazino, or any of the twenty standard amino acids bonded to the A ring via the amino-nitrogen atom. The methods comprise cyclizing a compound of Formula IV:

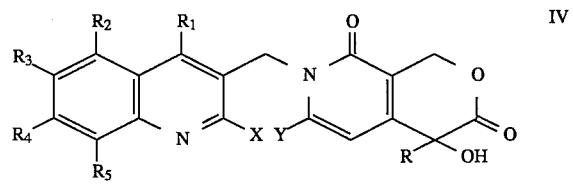

wherein X is Br or I, and Y is H, by an Aryl-to-Aryl free radical coupling reaction to yield a compound of Formula I. Compounds of Formula IV are made by alkylating a compound of Formula III:

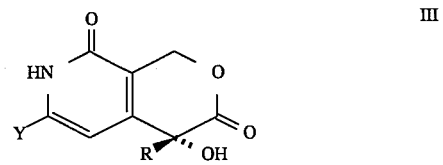

wherein R is loweralkyl and Y is H with a compound of Formula II-x:

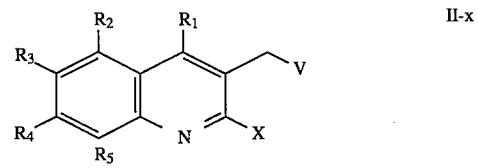

wherein X is a Br or I and V is hydroxy, by a Mitsunobu reaction to yield the compound of Formula IV.

7 Claims, No Drawings

CAMPTOTHECIN INTERMEDIATES AND METHOD OF MAKING CAMPTOTHECIN AND COMPTOTHECIN ANALOGS

FIELD OF THE INVENTION

The present invention relates to the parallel synthesis of camptothecin and camptothecin analogs via a Mitsunobu reaction and then an aryl-to-aryl intramolecular free radical coupling reaction.

BACKGROUND OF THE INVENTION

Camptothecin (Chem. Abstracts Registry No. 7689-03-4) is a naturally occurring compound found in Camptotheca acuminata (Nyssaceae) which has antileukemic and antitumor properties. Numerous camptothecin analogs having like properties are known, examples being those described in U.S. Pat. No. 4,894,456 to Wall et al. and European Patent Application No. 0 325 247 of Yaegashi et al.

A number of linear syntheses for camptothecin are known. Several routes are reviewed in *Natural Products Chemistry*, Vol. 2, 358–361 (K. Nakanishi, T. Goto, S. Itô, S. Natori and S. Nozoe eds.) and in J. Cai and C. Hutchinson, Camptothecin, in *The Alkaloids*, Vol. XXI, 101–137 (Academic Press 1983). The biosynthesis of camptothecin is described in *Natural Products Chemistry*, Vol. 3, 573–574 (K. Nakanishi et al. eds.). A recent synthetic route is described in U.S. Pat. No. 4,894,456 to Wall et al. (see also references cited therein).

Parallel syntheses, in which two synthetic paths are followed separately and the products thereof combined to form the final product, generally provide higher yields than linear syntheses. Parallel syntheses for camptothecin and camptothecin analogs is disclosed in U.S. Pat. Nos. 5,162,532 and 5,212,317. These patents disclose syntheses in which the camptothecin or camptothecin analog is produced via an intermediate of Formula IV:

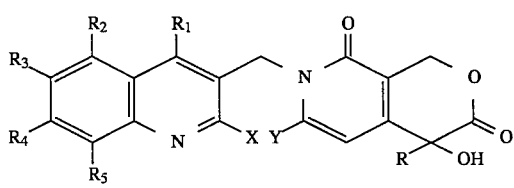

wherein R may be loweralkyl; $R_1$ may be H, loweralkyl, loweralkoxy, or halo; $R_2$, $R_3$, $R_4$ and $R_5$ may each independently be H, amino, hydroxy, loweralkyl, loweralkoxy, loweralkylthiol, di(loweralkyl)amino, cyano, methylenedioxy, formyl, nitro, halo, trifluoromethyl, aminomethyl, azido, amido, hydrazino, or any of the twenty standard amino acids bonded to the A ring via the amino-nitrogen atom; X is Br or I; and Y is H. The intermediate of Formula IV is then cyclized by an intramolecular Heck reaction in a polar aprotic solvent in the presence of a palladium catalyst to yield camptothecin or an analog thereof.

SUMMARY OF THE INVENTION

The present invention provides new techniques for the production of camptothecin and analogs thereof by parallel synthesis.

A first aspect of the present invention is, accordingly, a method of making a compound of Formula I:

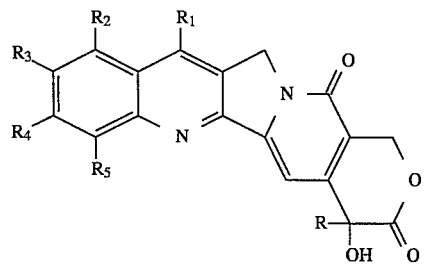

wherein:
R is loweralkyl;
$R_1$ is H, loweralkyl, loweralkoxy, or halo; and
$R_2$, $R_3$, $R_4$ and $R_5$ are each independently H, amino, hydroxy, loweralkyl, loweralkoxy, loweralkylthiol, di(loweralkyl)amino, cyano, methylenedioxy, formyl, nitro, halo, trifluoromethyl, aminomethyl, azido, amido, hydrazino, or any of the twenty standard amino acids bonded to the A ring via the amino-nitrogen atom, and where methylenedioxy comprises $R_2$ and $R_3$, $R_3$ and $R_4$, or $R_4$ and $R_5$ taken together. The method comprises cyclizing a compound of Formula IV:

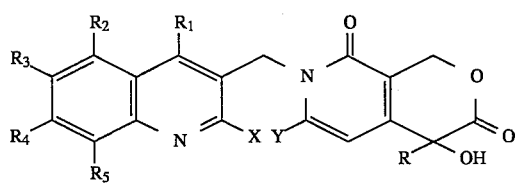

wherein X is Br or I and Y is H, by an Aryl-to-Aryl free radical coupling reaction in a substituted aryl solvent in the presence of a free radical initiator and a catalytic reducing agent to yield a compound of Formula I.

Also disclosed is a method of making a compound of Formula IV above comprising alkylating a compound of Formula III:

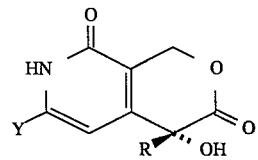

wherein is loweralkyl and Y is H with a compound of Formula II-x:

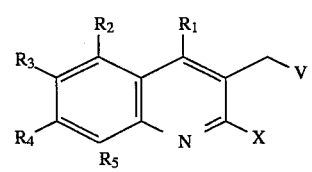

wherein X is Br or I and V is hydroxy, by a Mitsunobu reaction in an aprotic solvent in the presence of triphenylphosphine and diethyl azodicarboxylate to yield the compound of Formula IV.

The foregoing and other objects and aspects of the present invention are explained in detail in the specification hereinbelow.

DETAILED DESCRIPTION OF THE INVENTION

The present invention provides a method of making compounds of Formula I below:

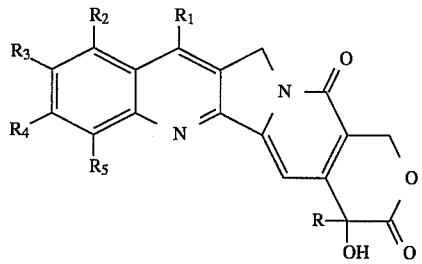

wherein:

R may be loweralkyl, preferably ethyl.

$R_1$ may be H, loweralkyl, loweralkoxy, or halo (e.g., chloro). Preferably $R_1$ is H.

$R_2$, $R_3$, $R_4$, and $R_5$ may each independently be H, amino, hydroxy, loweralkyl, loweralkoxy, loweralkylthio, di(loweralkyl)amino, cyano, methylenedioxy, formyl, nitro, halo, trifluoromethyl, aminomethyl, azido, amido, hydrazino, or any of the twenty standard amino acids bonded to the A ring via the amino-nitrogen atom (numbering in Formula I is by the Le Men-Taylor numbering system and rings are lettered in the conventional manner. See J. Cai and C. Hutchinson, supra at 102).

At least two of $R_2$, $R_3$, $R_4$, and $R_5$ may by H, and in a preferred embodiment $R_2$, $R_4$, and $R_5$ are H.

Preferably: $R_2$ is H or amino; $R_3$ is H or hydroxy; $R_4$ is H; and $R_5$ is H.

In the present invention, a camptothecin intermediate of Formula IV is produced by a new process involving a modified Mitsunobu reaction. In this process compounds of Formula III and a hydroxymethylquinoline of Formula II-x are combined and treated with diethyl azodicarboxylate and triphenylphosphine (the Mitsunobu reaction) to give the compound of Formula IV. For a review of the Mitsunobu reaction, see Misunobu, *Synthesis*, 1998, 1. Also see Martin and Dodge, *Tetrahedron Letters*, 32, 3017, 1991; Saiah et al., *Tetrahedron Letters*, 30, 4317, 1992. The C-ring of camptothecin is then closed using a novel free-radical reaction. This novel method of converting compound III and II-x to camptothecin occurs in 2 steps, as explained below.

As used herein, the term "loweralkyl" means a linear or branched alkyl group with 1–8, preferably 1–4, carbon atoms, such as methyl, ethyl, propyl, isopropyl, n-butyl, tert-butyl, hexyl, and octyl. This definition also applies to a loweralkyl moiety in the loweralkoxy, loweralkylthio, and di(loweralkyl)amino groups. Thus, examples of loweralkoxy groups are methoxy, ethoxy, propoxy, sec-butoxy, and isohexoxy; examples of loweralkylthio groups are methylthio, ethylthio, tert-butylthio, and hexylthio; and examples of di(loweralkyl)amino groups are dimethylamino, diethylamino, diisopropylamino, di(n-butyl)amino, and dipentylamino.

The terms "halo" and "halogen" as used herein refers to a substituent which may be fluoro, chloro, bromo, or iodo.

Substituents on the "A" ring of the compounds disclosed herein may be joined together to form a bifunctional substituent such as the methylenedioxy group. Methylenedioxy substituents may be bonded to any two consecutive positions in the A ring, for example, the 9,10, the 10,11, or the 11,12 positions.

Substituents which are standard amino acids may be any of the twenty amino acids commonly found in naturally occurring proteins, and are well known in the art. These provide a substituent of the formula —NHCHRCOOH, with R being the side chain of any of the twenty standard amino acids. The amino acids may be of any configuration, but preferably have an (L) configuration.

A compound of Formula I is produced in accordance with Scheme A below by by alkyating a pyridone of Formula III with a hydroxymethylquinoline of Formula II-X in a Mitsubonu reaction to produce a compound of Formula IV.

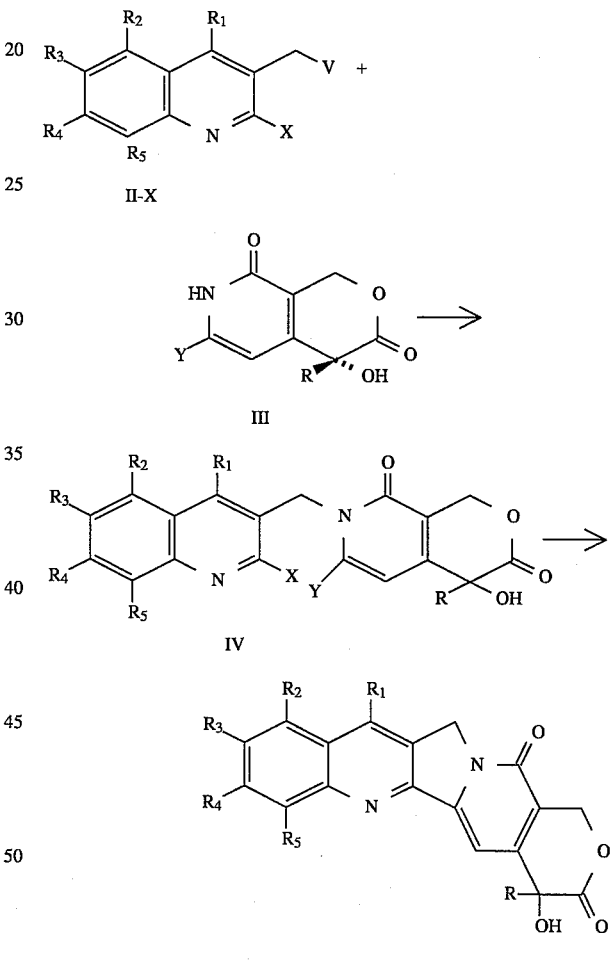

SCHEME A

In Scheme A: Y is H; R and $R_1$ through $R_5$ are as given in connection with Formula I above; X is Br or I; and V is hydroxy.

The Mitsunobu reaction of Scheme A involves treating the compounds of Formula II-x and III with diethyl azodicarboxylate and triphenylphosphine. The reaction may be carried out by adding diethyl azodicarboxylate dropwise to a solution containing the pyridone, the hydroxymethylquinoline and triphenylphosphine and stirring at, for example, ambient temperature for a sufficient time (e.g., 1–24 hours). The reaction may be carried out in a suitable solvent, such as an aprotic solvent (e.g., tetrahydrofuran, 1,2-dimethoxyethane, toluene, acetonitrile, dimethylformamide, benzene or methylene chloride) and is preferably carried out under neutral conditions.

The compound of Formula IV may be cyclized to yield the compound of Formula I by a free-radical reaction. This free radical Aryl to Aryl coupling with a 2-pyridone is novel. Free-radical Aryl to Aryl couplings have been reported but not with 2-pyridones. See "Radicals in Organic Synthesis: Formation of Carbon-Carbon Bonds", Chapter 5, B. Giese (Ed), Pergamon Press (1986). The present cyclization reaction, which closes the C-ring of the compound of Formula IV, occurs in two stages, first, a solution of toluene and tributyltin hydride, are heated to reflux, and then a solution of 2,2'-azobisisobutyronitrile and the compound of Formula IV in toluene are added over 1–24 hours.

The compounds of Formula II-x may be prepared in accordance with Scheme B below, where $R_1-R_5$ are as given in connection with Formula I, above.

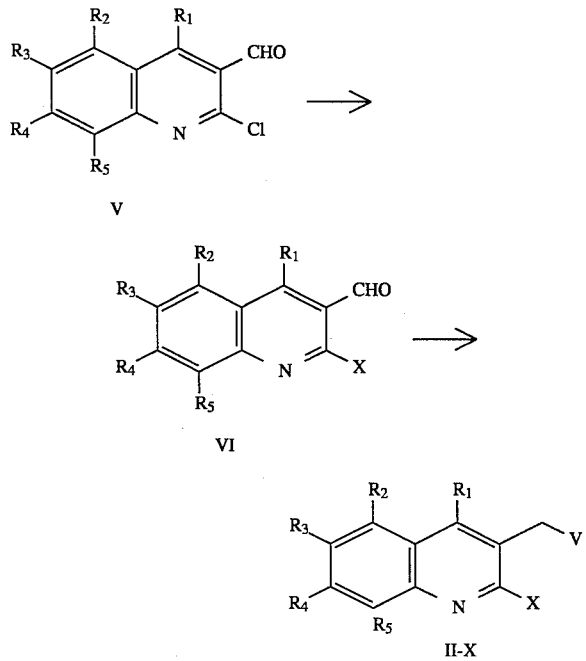

The starting materials of Scheme B (the compounds of Formula V) are made by known techniques, such as by chlorination of a quinoline. See, e.g., *Progress in Heterocyclic Chemistry* 2, 180 (H. Suschitzky and E. Scriven eds. 1990). In the alternative, compounds of Formula V may be made from the substituted acetanilide as described by O. Meth-Coyn et al., *J. Chem. Soc. Perkin Trans.* I 1981, 1520.

The halo group on the carboxaldehyde of Formula V is exchanged with a bromo to produce the carboxaldehyde of Formula VI. The exchange reaction may be carried out in acetonitrile in the presence of a catalytic amount of a strong acid, such as HCl, by heating the reaction mixture to between about 70° to about 90° C. for at least about 4 hours.

The carboxaldehyde of Formula VI is then reduced to produce the hydroxymethylquinoline of Formula II-x. The reaction is carried out with a mild reducing agent to avoid reducing the quinoline ring, at a temperature of from about 0° to about 25° C., in an alcohol solvent. An alternative route for producing a compound of Formula II-x is disclosed in N.

Narasimham et al., *J. Chem. Soc., Chem. Commun.*, 1985, 1368–1369.

The compounds of Formula III above may be prepared as described in U.S. Pat. No. 5,162,532 or, for an asymetric synthesis, as described in Scheme E of U.S. Pat. No. 5,212,317 (applicant specifically intends that the disclosures of these and all other patent references cited herein be incorporated herein in their entirety). Compounds of Formula III may also be prepared in the manner described in D. Comins, Ph.D. Thesis, University of New Hampshire, Durham, N.H., at 25–29 (1977), and as described in Lyle et al., *J. Org. Chem.* 38, 3268–3271 (1973).

The discussion herein is, for simplicity, given without reference to sterioisomerism. However, the compounds of Formula I have an asymmetric carbon atom at the C-20 position. Thus, the present invention is concerned with the synthesis of both (i) racemic mixtures of the compound of Formula I and (ii) enantiomeric forms of the compound of Formula I, particularly the 20-(S) form. The resolution of racemates into enantiomeric forms can be done in connection with the last step of the process, or in preceeding steps involving the asymmetric synthesis of an intermediate having an asymmetric carbon atom, by known procedures, as noted above. For example, the racemate may be converted with an optically active reagent into a diasteriomeric pair, and the diasteriomeric pair subsequently separated into the enantiomeric forms.

Specific examples of compounds which may be prepared by the method of the presen invention include 9-methoxy-camptothecin, 9-hydroxy-camptothecin, 9-nitro-camptothecin, 9-amino-camptothecin, 10-hydroxy-camptothecin, 10-nitro-camptothecin, 10-amino-camptothecin, 10-chloro-camptothecin, 10-methyl-camptothecin, 11-methoxy-camptothecin, 11-hydroxy-camptothecin, 11-nitro-camptothecin, 11-amino-camptothecin, 11-formyl-camptothecin, 11-cyano-camptothecin, 12-methoxy-camptothecin, 12-hydroxy-camptothecin, 12-nitro-camptothecin, 10,11-dihydroxy-camptothecin, 10,11-dimethoxy-camptothecin, 7-methyl-10-fluoro-camptothecin, 7-methyl-10-chloro-camptothecin, 7-methyl-9,12-dimethoxy-camptothecin, 9,10,11-trimethoxy-camptothecin, 10,11-methylenedioxy-camptothecin and 9,10,11,12-tetramethyl-camptothecin.

Compounds of Formula I have antitumor and antileukemic activity. Additionally, compounds of Formula I wherein $R_1$ is halo are useful as intermediates for, among other things, making compounds of Formula I wherein $R_1$ is loweralkyl.

Those skilled in the art will appreciate that additional changes can be made in the compounds of Formula I (see, for examples, J. Cai and C. Hutchinson, supra), which changes will not adversely affect the new processes disclosed herein and do not depart from the concept of the present invention.

In the Examples which follow, "mg" means milligrams, "g" means grams, "M" means Molar, mL means millimeter(s), "mmol" means millimole(s), "Bu" means butyl, "THF" means tetrahydrofuran, "h" means hours, "min" means minutes, "C" means Centigrade, "p.s.i". means pounds per square inch, "DMF" means dimethylformamide, "TLC" means thin layer chromatography, "LDA" means lithium diisopropylamide, "EtoAc" means ethyl acetate, and "PLC" means preparative thin layer chromatography.

EXAMPLE 1

Preparation of 2-Bromo-3-(hydroxymethyl)quinoline(Compound II-x)

To a solution of LDA, freshly prepared from diisopropylamine (0.42 mL, 2.97 mmol) and n-BuLi (2.97 retool), in THF (10 mL) at −78° C. was added 2-bromoquinoline (T. Young and E. Amstutz, *J. Am. Chem. Soc.* 73, 4773 (1951)) (570 mg, 2.7 mmol) and stirring was continued for 1 h. This mixture was cannulated into a solution of formaldehyde in THF at −78° C., which was prepared by cracking paraformaldehyde (1.24 g, 14.8 mmol) under 140°–180° C. and releasing the gas into THF (25 mL) at −23° C. Stirring was continued for 6.5 h at −78° C. The reaction was quenched with water (5 mL) and extracted with EtOAc (3×25 mL). After drying (MgSO$_4$), concentration gave a light yellow solid (660 mg) which was purified by recrystallization and chromatography (silica gel, 15% EtOAc/hexanes) to give 373 mg (58%) of the product as a white solid: mp 173°–4° C. $^1$H NMR (300 MHz, CDCl$_3$) δ8.24 (s, 1H), 8.05 (d, 1H, J=8 Hz), 7.84 (d, 1H, J=8 Hz), 7.75 (m, 1H), 7.59 (m, 1H). 4.90 (d, 2H, J=6 Hz), 2.36 (rt, 1H, J=6 Hz). Analysis calculated for C$_{10}$H$_8$BrNO was as follows: C, 50.45; H, 3.39; N, 5.88. Found: C, 50.72; H, 3.35; N, 5.94.

EXAMPLE 2

Preparation of 8-(2'-bromo-3'-quinolymethyl)-7-oxopyrido[5,4-c]-2-oxo-3-ethyl-3-hydroxy-3,6-dihydropyran (Compound IV) by the Mitsunobu Reaction To a solution containing 7-oxopyrido[5,4-c]- -2-oxo-3-ethyl-3-hydroxy-3,6-dihydropyran (20 mg, 0.08 mmol), 2-bromo-3-hydroxymethylquinoline (21 mg, 0,088 mmol) and triphenylphosphine (31 mg, 0.12 mmol) in THF (5 mL) was added diethyl azodicarboxylate (21 μL, 0.12 mmol) dropwise at ambient temperature. The light yellow solution was stirred for 8 h at ambient temperature. The reaction was quenched by adding MeOH (1 mL) and water (2 mL). After 5 min, an additional 3 mL of water was added and the layers were separated. The aqueous layer was extracted with methylene chloride (4×10 mL). The combined organic layers were washed with water and brine. The light yellow residue obtained from concentration of the dried organic layer (MgSO$_4$) in vacuo was purified by radial PLC (silica gel, MeOH/CH$_2$C$_1$Cl$_2$/hexanes, 2:48:50) to give 31 mg (84%) of IV, as a white solid. A sample was recrystallized from 1:1 CH$_2$Cl$_2$/acetone: mp 242°–244° C. (dec.); $^1$H NMR (300 MHz, CDCl$_3$) δ8.04 (d, 1 H), 7.55–7.95 (m, 5H), 6.60 (d, 1H), 5.08–5.70 (m 4H), 1.82 (m, 2H), 0.99 (t, 3H, J=7 Hz); $^{13}$C NMR (75 MHz, CDCl$_3$) δ170.9, 156.5, 147.9, 145.5, 140.2, 136.8, 135.0, 129.0, 128.1, 126.3, 126.0, 125.8, 125.2, 117.4, 101.6, 70.2, 63.8, 49.8, 29.2, 6.0. Analysis calculated for C$_{20}$H$_{17}$BrNO$_4$ was as follows: C, 55.96; H, 3.99; N, 6.53. Found: C, 56.06; H, 4.02; N, 6.55.

EXAMPLE 3

Cyclization of Compound IV to Give Camptothecin

To a stirred mixture of tributyltin hydride (30 mg, 0.1 mmol) in 1 mL of toluene at reflux was added a solution of 20 mg (0.047 mmol) of 8-(2'-bromo-3'-quinolymethyl-7-oxopyrido [5,4-c]-2-oxo-3-ethyl-3 -hydroxy-3,6-dihydropyran and 6 mg (0,047 mmol) of AIBN in 5 mL of toluene over 5 hours by using a syringe pump. Heating was continued for 1 hour, and the mixture was cooled to room temperature and concentrated under reduced pressure. A solution of 30 mL of 5% MeOH/CH$_2$Cl$_2$ was added to dissolve the residue. The mixture was washed with water and brine, and was dried over magnesium sulfate. Concentration gave the crude product which was purified by radial preparative-layer chromatography (silica gel, 1% MeOH/CH$_2$C$_2$) to give 9 mg (55%) of (±)-camptothecin, mp 273°–275° C.(mp 275°–277° C. reported in Volman, R.; Danishefsky, S.;Eggler, J.; Soloman, D. M. *J. Am. Chem. Soc.* 97, 93, 4074.).

The foregoing examples are illustrative of the present invention, and are not to be construed as limiting thereof. The invention is defined by the following claims, with equivalents of the claims to be included therein.

That which is claimed is:

1. A method of making a compound of Formula I

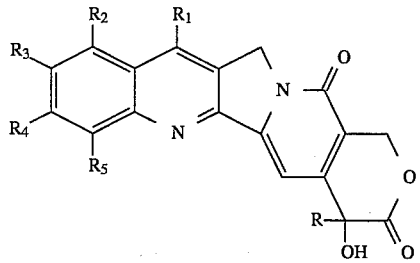

wherein:
R is loweralkyl;
R$_1$ is H, loweralkyl, loweralkoxy, or halo; and
R$_2$, R$_3$, R$_4$ and R$_5$ are each independently H, amino, hydroxy, loweralkyl, loweralkoxy, loweralkylthiol, di(loweralkyl)amino, cyano, methylenedioxy, formyl, nitro, halo, trifluoromethyl, aminomethyl, azido, amido, hydrazino, or any of the twenty standard amino acids bonded to the A ring via the amino-nitrogen atom, and where methylenedioxy consists of R$_2$ and R$_3$, R$_3$ and R$_4$, or R$_4$ and R$_5$ taken together;
said method comprising cyclizing a compound of Formula IV:

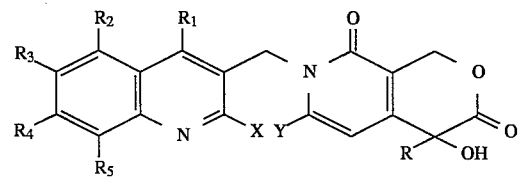

wherein:
Y is H;
X is Br or I;
said cyclizing comprising an Aryl-to-Aryl free radical coupling reaction in an aryl solvent substituted 1–3 times with a loweralkyl in the presence of a free radical initiator and a reducing agent capable of effecting cyclization selected from the group consisting of tributyltin hydride, triphenyltin hydride, tributylgermanium hydride, triphenylgermanium hydride, and tris(trimethylsilyl)-silane, to yield the compound of Formula I.

2. A method according to claim 1 wherein the aryl solvent is selected from the group consisting of benzene, toluene, trimethylbenzene, triethylbenzene, tributylbenzene, and tert-butylbenzene.

3. A method according to claim 1 wherein the aryl solvent is toluene.

4. A method according to claim 1 wherein the free radical initiator is 2,2'-azobisisobutyro-nitrile.

5. A method according to claim 1 wherein the reducing agent capable of effecting cyclization is tributyltin-hydride.

6. A method according to claim 1, wherein said Aryl-to-Aryl free radical coupling reaction is carried out by:

(a) refluxing a reducing agent selected from the group consisting of tributylin hydride, triphenylin hydride, tributylgermanium hydride, triphenylgermanium hydride, and tris(trimethylsilyl)-silane, in the presence of an aryl solvent substituted 1–3 times with a loweralkyl; and (b) adding the compound of Formula IV with 2,2'-azobisisobutyronitrile in the presence of benzene or an aryl solvent substituted 1–3 times with a loweralkyl.

7. A method of making a compound of Formula I

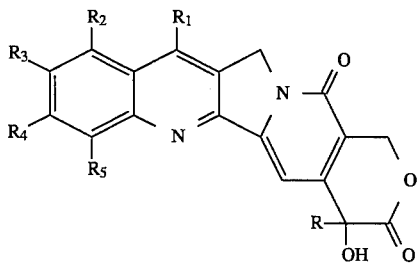

wherein:
R is loweralkyl;
$R_1$ is H, loweralkyl, loweralkoxy, or halo; and
$R_2$, $R_3$, $R_4$ and $R_5$ are each independently H, amino, hydroxy, loweralkyl, loweralkoxy, loweralkylthiol, di(loweralkyl)amino, cyano, methylenedioxy, formyl, nitro, halo, trifluoromethyl, aminomethyl, azido, amido, hydrazino, or any of the twenty standard amino acids bonded to the A ring via the amino-nitrogen atom, and where methylenedioxy consists essentially of $R_2$ and $R_3$, $R_3$ and $R_4$, or $R_4$ and $R_5$ taken together;

said method comprising cyclizing a compound of Formula IV:

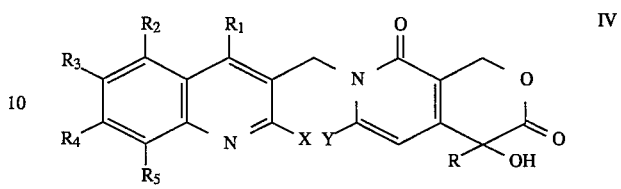

wherein:
Y is H;
X is Br or I;
said cyclizing comprising an Aryl-to-Aryl free radical coupling reaction carried out by:
(a) refluxing a mixture comprising
 (i) a reducing agent selected from the group consisting of tributyltin hydride, triphenyltin hydride, tributylgermanium hydride, triphenylgermanium hydride, and tris(trimethylsilyl)silane, and
 (ii) a solvent selected from the group consisting of benzene, toluene, trimethylbenzene, triethylbenzene, tributylbenzene, and tert-butylbenzene; and
(b) adding the compound of Formula IV and 2,2'-azobisisobutyronitrile to said mixture to yield a compound of Formula I.

* * * * *